United States Patent
Vacanti et al.

Patent Number: 6,027,744
Date of Patent: Feb. 22, 2000

[54] GUIDED DEVELOPMENT AND SUPPORT OF HYDROGEL-CELL COMPOSITIONS

[75] Inventors: Charles A. Vacanti; Joseph P. Vacanti, both of Worcester, Mass.

[73] Assignees: University of Massachusetts Medical Center; The Children's Medical Center Corporation, both of Boston, Mass.

[21] Appl. No.: 09/066,038

[22] Filed: Apr. 24, 1998

[51] Int. Cl.⁷ ................... A61F 2/02; A61F 2/28
[52] U.S. Cl. ................... 424/426; 623/12; 623/16
[58] Field of Search ............... 424/426; 623/12, 623/16

[56] References Cited

U.S. PATENT DOCUMENTS

| | | |
|---|---|---|
| 4,191,747 | 3/1980 | Scheicher ................................. 424/94 |
| 4,846,835 | 7/1989 | Grande ....................................... 623/16 |
| 4,997,443 | 3/1991 | Walthall et al. .......................... 623/11 |
| 5,041,138 | 8/1991 | Vacanti et al. ............................ 623/16 |
| 5,071,644 | 12/1991 | Viegas et al. ........................ 514/772.7 |
| 5,082,670 | 1/1992 | Gage et al. . |
| 5,126,141 | 6/1992 | Henry ....................................... 424/423 |
| 5,192,326 | 3/1993 | Bao et al. ................................. 623/17 |
| 5,277,911 | 1/1994 | Viegas et al. ............................ 424/427 |
| 5,292,516 | 3/1994 | Viegas et al. ............................ 424/423 |
| 5,294,446 | 3/1994 | Schlameus et al. ..................... 424/489 |
| 5,298,260 | 3/1994 | Viegas et al. ............................ 424/486 |
| 5,300,295 | 4/1994 | Viegas et al. ............................ 424/427 |
| 5,306,501 | 4/1994 | Viegas et al. ............................ 424/423 |
| 5,318,780 | 6/1994 | Viegas et al. ............................ 424/427 |
| 5,405,366 | 4/1995 | Scheicher ................................. 424/94 |
| 5,410,016 | 4/1995 | Hubbell et al. ......................... 528/354 |
| 5,443,950 | 8/1995 | Naughton et al. . |
| 5,512,600 | 4/1996 | Mikos et al. . |
| 5,514,378 | 5/1996 | Mikos et al. . |
| 5,529,914 | 6/1996 | Hubbell et al. . |

(List continued on next page.)

FOREIGN PATENT DOCUMENTS

| | | |
|---|---|---|
| 0 361 957 | 4/1990 | European Pat. Off. . |
| WO 92/06702 | 4/1992 | WIPO . |
| WO92/06702 | 4/1992 | WIPO . |
| Wo 93/16687 | 2/1993 | WIPO . |
| WO93/24627 | 12/1993 | WIPO . |
| WO94/25079 | 11/1994 | WIPO . |
| WO94/25080 | 11/1994 | WIPO . |
| WO96/40304 | 12/1996 | WIPO . |
| WO98/30678 | 7/1998 | WIPO . |

OTHER PUBLICATIONS

Frederiksen et al., "Proliferation and Differentiation of Rat Neuroepithelial Precursor Cells In Vivo," The Journal of Neuroscience, 8:1144–1151, Apr. 1988.

Ferringa et al., "Regeneration of Corticospinal Axons in the Rat," Annals of Neurology, 2:315–321, Oct. 1977.

(List continued on next page.)

*Primary Examiner*—Carlos A. Azpuru
*Attorney, Agent, or Firm*—Fish & Richardson P.C.

[57] ABSTRACT

The invention features a method for generating new tissue, the method including: obtaining a liquid hydrogel-cell composition including a hydrogel and tissue precursor cells; delivering the liquid hydrogel-cell composition into a permeable, biocompatible support structure; and allowing the liquid hydrogel-cell composition to solidify within the support structure and the tissue precursor cells to grow and generate new tissue. The invention also features a tissue forming structure including: a permeable, biocompatible support structure having a predetermined shape that corresponds to the shape of desired tissue; and a hydrogel-cell composition at least partially filling the support structure, wherein the hydrogel-cell composition comprises a hydrogel and tissue precursor cells.

39 Claims, 5 Drawing Sheets

6,027,744

U.S. PATENT DOCUMENTS

| | | |
|---|---|---|
| 5,567,612 | 10/1996 | Vacanti et al. ............... 435/240.23 |
| 5,575,815 | 11/1996 | Slepian et al. ............... 623/11 |
| 5,578,485 | 11/1996 | Naughton et al. . |
| 5,589,376 | 12/1996 | Anderson et al. . |
| 5,593,974 | 1/1997 | Rosenberg et al. ............... 514/44 |
| 5,667,778 | 9/1997 | Atala . |
| 5,696,175 | 12/1997 | Mikos et al. . |
| 5,709,854 | 1/1998 | Griffith-Cima et al. . |
| 5,716,404 | 2/1998 | Vacanti et al. . |
| 5,736,372 | 4/1998 | Vacanti et al. ............... 435/180 |
| 5,750,376 | 5/1998 | Weiss et al. . |
| 5,753,506 | 5/1998 | Johe . |
| 5,759,830 | 6/1998 | Vacanti et al. ............... 435/180 |
| 5,762,926 | 6/1998 | Gage et al. . |
| 5,770,193 | 6/1998 | Vacanti et al. ............... 424/93.7 |
| 5,770,417 | 6/1998 | Vacanti et al. ............... 435/180 |
| 5,786,216 | 7/1998 | Dionne et al. ............... 435/402 |
| 5,795,790 | 8/1998 | Schinstine et al. . |
| 5,804,178 | 9/1998 | Vacanti et al. . |
| 5,827,735 | 10/1998 | Young et al. . |
| 5,830,651 | 11/1998 | Cauley et al. . |
| 5,834,029 | 11/1998 | Bellamkonda et al. . |
| 5,851,832 | 12/1998 | Weiss et al. . |
| 5,855,610 | 1/1999 | Vacanti et al. . |

OTHER PUBLICATIONS

Gage et al., "Survival and Differentiation of Adult Neuronal Progenitor Cells Transplanted to the Adult Brain," Proc. Natl. Acad. Sci. USA, 92:11879–11883, Dec. 1995.

Houle et al., "Bridging a Complete Transection Lesion of Adult Rat Spinal Cord with Growth Factor–Treated Nitrocellulose Implants," Journal of Neural Transplantation & Plasticity, 5:115–124, 1994.

Lachyankar et al., "Embryonic Precursor Cells that Express Trk Receptors: Induction of Different Cell Fates by NGF, BDNF, NT–3, and CNTF," Experimental Neurology, 144:350–360, 1997.

Morshead et al., "Neural Stem Cells in the Adult Mammalian Forebrain: A Relatively Quiescent Subpopulation of Subependymal Cells," Neuron, 13:1071–1082, Nov. 1994.

Ray et al., "Proliferation, Differentiation, and Long–Term Culture of Primary Hippocampal Neurons," Proc. Natl. Acad. Sci. USA, 90:3602–3606, Apr. 1993.

Ray et al., "Spinal Cord Neuroblasts Proliferate in Response to Basic Fibroblast Growth Factor," The Journal of Neuroscience, 14:3548–3564, Jun. 1994.

Reynolds et al., "Clonal and Population Analyses Demonstrate that an EGF–Responsive Mammalian Embryonic CNS Precursor is a Stem Cell," Developmental Biology, 175:1–13, 1996.

Reynolds et al., "Generation of Neurons and Astrocytes from Isolated Cells of the Adult Mammalian Central Nervous System," Science, 255:1707–1710, Mar. 27, 1992.

Reynolds et al., "A Multipotent EGF–Responsive Striatal Embryonic Progenitor Cell Produces Neurons and Astrocytes," The Journal of Neuroscience, 12:4565–4574, Nov. 1992.

Shihabuddin et al., "The Adult CNS Retains the Potential to Direct Region–Specific Differentiation of a Transplanted Neuronal Precursor Cell Line," The Journal of Neuroscience, 15:6666–6678, Oct. 1995.

Shihabuddin et al., "FGF–2 is Sufficient to Isolate Progenitors Found in the Adult Mammalian Spinal Cord," Experimental Neurology, 148:577–586, 1997.

Shihabuddin et al., "Induction of Mature Neuronal Properties in Immortalized Neuronal Precursor Cells Following Grafting into the Neonatal CNS," Journal of Neurocytology, 25:101–111, 1996.

Craig et al., "In Vivo Growth Factor Expansion of Endogenous Subependymal Neural Precursor Cell Populations in the Adult Mouse Brain," The Journal of Neuroscience, 16:2649–2658, Apr. 15, 1996.

Davis et al., "A Self–Renewing Multipotential Stem Cell in Embryonic Rat Cerebral Cortex," Nature, 372:263–269, Nov. 17, 1994.

Stanton et al., "The Growth of Chondrocytes Using Gelfoam® as a Biodegradable Scaffold," Journal of Materials Science: Materials in Medicine 6, 739–744, 1996.

Suhonen et al., "Differentiation of Adult Hippocampus––Derived Progenitors into Olfactory Neurons in Vivo," Nature, 383:624–627, Oct. 17, 1996.

Taylor et al., "Widespread Engraftment of Neural Progenitor and Stem–Like Cells Throughout the Mouse Brain," Transplantation Proceedings, 29:845–847, 1997.

Weiss et al., "Multipotent CNS Stem Cells are Present in the Adult Mammalian Spinal Cord and Ventricular Neuroaxis," The Journal of Neuroscience, 16:7599–7609, Dec. 1, 1996.

GUIDED DEVELOPMENT AND SUPPORT OF HYDROGEL-CELL COMPOSITIONS

FIELD OF THE INVENTION

The invention relates to methods of generating tissue such as cartilage, bone, skin, organs, and epithelial layers, to repair or replace tissue damaged by disease or injury, augment existing tissue, or create tissue not originally present.

BACKGROUND OF THE INVENTION

There is much interest within the medical community for methods and materials for use in reconstructive surgery of tissue. An emerging approach is tissue engineering, in which new tissue is grown from tissue-precursor cells and engineered into desired shapes and structures. The types of tissues that can be grown and engineered include, for example, bone, cartilage, and nervous system tissue.

One of the primary uses for replacement cartilage is to correct defects in the articular surface of various joints. For example, a damaged cartilage meniscus in a patient's knee can be replaced with an artificially engineered meniscus. See, for example, U.S. Pat. No. 5,041,138 (Vacanti et al.). In other examples of tissue engineering, hollow spaces or lumens within tissues can be filled with tissue-precursor cells suspended in, for example, gelatin, collagen, fibrin, or various hydrogels. See, for example, International Patent Application WO 94/25080 entitled "Injectable polysaccharide-cell compositions" (Griffith-Cima et al.).

SUMMARY OF THE INVENTION

The invention features a method of generating new tissue in a patient by delivering a liquid hydrogel-cell composition, which contains a hydrogel and tissue precursor cells, into a permeable, biocompatible support structure. The hydrogel-cell composition fills the permeable support structure and takes the shape of the support structure as the composition solidifies and new tissue is formed as the cells grow and multiply. After being saturated with the hydrogel-cell composition, the support structure can be implanted into a patient. Alternatively, the support structure can be filled with the liquid hydrogel-cell composition after it is implanted into the patient. For example, the support structure can be implanted and subsequently injected with the hydrogel-cell composition using a syringe or catheter. The support structure is shaped to corresponded to the desired tissue to be grown, e.g., a bone, a meniscus for a knee, an ear, an organ, a nose, or other tissue, e.g., cartilaginous tissue.

The combination of suspending the tissue precursor cells in the hydrogel and delivering the hydrogel-cell composition into a support structure profoundly improves the quality of the new tissue growth and the range of tissue shapes and structures that can be grown. The hydrogel-cell composition forms a uniform distribution of cells with a well-defined and precisely controllable density. Moreover, the hydrogel can support very large densities of cells, e.g., 50 million cells/ml. These factors improve the quality and strength of the new tissue. In addition, the hydrogel allows diffusion of nutrients and waste products to, and away from, the cells, which promotes tissue growth.

The support structure provides support for the hydrogel-cell composition and guides the development and shape of the growing tissue, which fills the support structure. Since it is the hydrogel that sustains and suspends the tissue precursor cells, rather than the support structure, the support structure can have any shape or structure from a wide range of shapes and structures. In particular, suitable support structures are sufficiently permeable to carry the hydrogel-cell composition and allow the exchange of nutrients and waste products between the hydrogel within the support structure and bodily fluids outside the support structure. Furthermore, the support structures can be biodegradable or biocompatible. Examples of support structures include sponges, foams, corals, rigid inorganic, ceramic, or metal structures having internal pores such a honeycomb structure made from titanium, a skeleton of fine struts, such as a mesh of thin interwoven polymer fibers, and a skeleton of thick struts, such as a network of metal, inorganic, ceramic, or plastic rods.

In general, in one aspect, the invention features a method for generating new tissue, the method including: obtaining a liquid hydrogel-cell composition including a hydrogel and tissue precursor cells; delivering the liquid hydrogel-cell composition into a permeable, biocompatible support structure; and allowing the liquid hydrogel-cell composition to solidify within the support structure and the tissue precursor cells to grow and generate new tissue.

The liquid hydrogel-cell composition can be delivered to the support structure by injecting the liquid composition into the support structure.

The method can further include implanting the support structure into an animal, e.g., a mammal such as a human. After the support structure is implanted into the animal, the hydrogel-cell composition can be delivered to the support structure.

In another aspect, the invention features a tissue forming structure that includes: a permeable, biocompatible support structure having a predetermined shape that corresponds to the shape of desired tissue; and a hydrogel-cell composition at least partially filling the support structure, wherein the hydrogel-cell composition includes a hydrogel and tissue precursor cells.

For example, the cells can be bone forming cells and the support structure can include porous hydroxyapatite. Also, the hydrogel-cell composition can be a solidified suspension of hydrogel supporting dispersed tissue precursor cells.

The method and tissue forming structure can include any of the following features.

The support structure can include any of ceramic material, metal, sponge, foam, porous hydroxyapatite, a mesh of fibers, and various polymers. For example, the support structure can be formed from polyanhydride, polyorthoester, polyglycolic acid, polylactic acid, or polyglactin. Also, the support structure can be compressible or rigid.

The support structure can be shaped in the form of desired tissue, such as in the form of articular cartilage adjacent a joint, a bone, a portion of a bone, or a bone defect. The support structure can also be biodegradable.

The hydrogel can include any of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

The tissue precursor cells can include any of the following: epidermal cells, chondrocytes and other cells that form cartilage, macrophages, dermal cells, muscle cells, hair follicles, fibroblasts, organ cells, osteoblasts and other cells that form bone, endothelial cells, mucosal cells, pleural cells, ear canal cells, tympanic membrane cells, peritoneal cells, Schwann cells, corneal epithelial cells, gingiva cells, neural cells, neural stem cells, tracheal epithelial cells, hepatocytes, pancreatic cells, and cardiac cells A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the cells at the application site, thereby eliminating problems of phagocytosis or cellular death and enhancing new cell growth at the application site. The hydrogels are also biocompatible, e.g., not toxic, to cells suspended in the hydrogel.

A "hydrogel-cell composition" is a suspension of a hydrogel containing desired tissue precursor cells. These cells can be isolated directly from a tissue source or can be obtained from a cell culture. A "tissue" is a collection or aggregation of particular cells embedded within its natural matrix, wherein the natural matrix is produced by the particular living cells. "Tissue precursor cells" are cells that form the basis of new tissue. Tissue cells can be "organ cells," which include hepatocytes, islet cells, cells of intestinal origin, cells derived from the kidney, cells of hair follicles, cells from the vitreous humor in the eyes, cells from the brain, and other cells acting primarily to synthesize and secret, or to metabolize materials.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. All publications, patent applications, patents, and other references mentioned herein are incorporated by reference in their entirety. In case of conflicting subject matter, the present specification, including definitions, will control. In addition, the materials, methods, and examples are illustrative only and not intended to be limiting.

The invention has many advantages. For example, upon gelling, the hydrogel-cell composition is supported by the support structure and forms a uniform suspension in which nutrients can readily diffuse to the cells and waste products can diffuse away from the cells. As a result, the hydrogel keeps the cells viable and allows vascularization of the suspension, ultimately resulting in the growth of new tissue and its engraftment to the patient's body. The permeable support structure, into which the liquid hydrogel-cell composition is delivered, provides a shape and structure for the solidifying hydrogel-cell composition while still allowing nutrients and waste products to diffuse to and from the cells within the hydrogel. Thus, the support structure guides the development and shape of the new tissue, and does so with the ability to resist external stresses from the environment and surrounding tissues, i.e., the support structure is immediately weight-bearing, for example if the structure is used to replace a bone or cartilage. Moreover, the weight bearing characteristic of the support structure in bone or cartilage enables stresses to be transmitted across the hydrogel-cell suspension that will encourage bone or cartilage development in the hydrogel-cell suspension.

In the absence of such a support structure, a patient would not be able to apply any weight or stress to the hydrogel-cell composition because such forces would cause the hydrogel-cell composition to become distorted and displaced. This is similar with any replacement of structural tissues which are exposed to stress, such as ligaments, tendons, and bones anywhere within the body. Note also that the support structure accommodates not only compressive forces but also tensile forces, such as when one pulls on a tendon or stretches skin. In such cases, the support structure mimics the elasticity of the tendon or skin, and has ends that are typically sutured or adhered to adjacent tissue.

Also, the support structure maintains the structural integrity and the desired shaped of the hydrogel-cell composition without altering the physical characteristics of the hydrogel-cell composition in ways that can harm the cells and limit the diffusion of nutrients and waste products to and from the cells.

Furthermore, the support structure can be designed to be compressible and resilient so that it can be easily implanted into a patient through, for example, a cannula, endoscope, or arthroscope. Thus, the support structure can be cut or molded into the shape of the desired tissue to be grown, implanted into the patient in a deformed state through a cannula, allowed to expand within the desired body cavity, and subsequently injected with the liquid hydrogel-cell composition. The subsequent growth of new tissue will take the shape of the support structure.

Other features and advantages of the invention will be apparent from the following detailed description, and from the claims.

DETAILED DESCRIPTION

Figure 1:
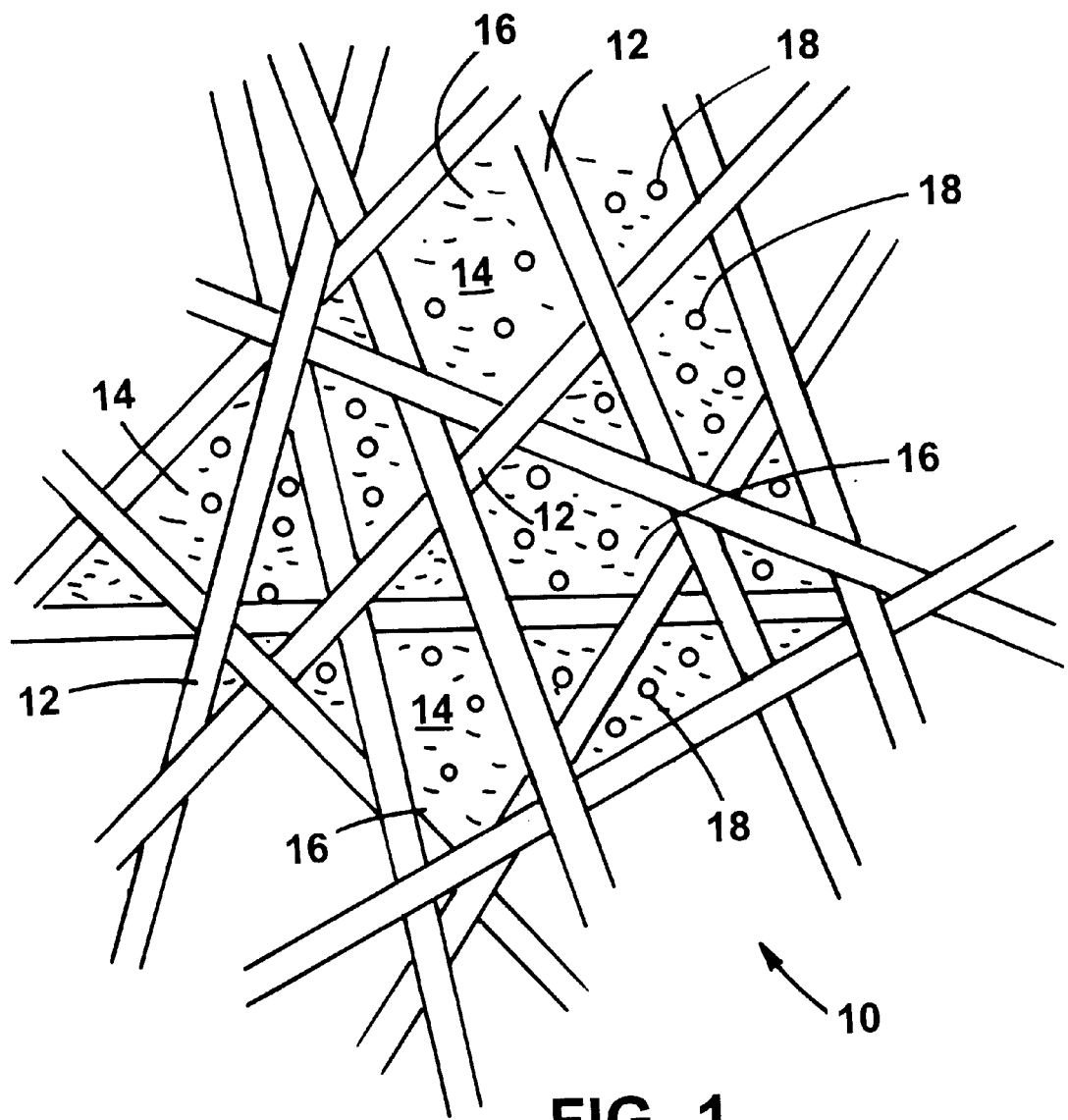
FIG. 1 is a schematic of a permeable support structure filled with a hydrogel-cell composition.

The invention provides methods of, and compositions for, growing new tissue such as, for example, cartilage, bone, skin, epithelial layers, new organs, and central nervous system tissue including brain tissue, spinal cord tissue, and peripheral nerves, by using a hydrogel-cell composition. To guide the development and shape of the new tissue, the hydrogel-cell composition is delivered into a permeable support structure, which is implanted into a patient either before or after the hydrogel-cell composition is delivered to the support structure. In the following subsections, suitable support structures, hydrogels, cells, and delivery methods will be described, along with illustrative examples.

Support Structures

The support structure provides the shape and support for the solidifying hydrogel-cell composition. It is permeable, typically having pore-like cavities or interstices that are filled by the liquid-hydrogel composition. For example, the support structure can be a porous polymer mesh, a natural or synthetic sponge, a piece of coral or hydroxyapatite having a desired porosity, or a matrix of metallic, inorganic, ceramic, or plastic struts. The permeability of the support structure allows diffusion of nutrients outside the structure into the hydrogel-cell composition filling the support structure (i.e., where the cells are) and the diffusion of waste products produced by the cells out of the structure through the hydrogel-cell composition, thereby promoting growth of the cells in the hydrogel-cell composition. Although other liquids, e.g., body fluids, may occupy the support structure prior to being filled with the liquid hydrogel-cell composition, the hydrogel-cell composition will displace these liquids and rapidly harden within the support structure.

The support structure is shaped in the form of the tissue to be grown. For example, the support structure can be shaped as a piece of cartilaginous tissue, such as a meniscus for a knee or elbow, a piece of bone to repair a bone defect, an ear, a nose, an internal organ, a ligament, a tendon, the trachea (as a conduit), mandibles, or skin. Depending on the material from which it is made, the support structure can be shaped by cutting, molding, or casting, or any other method that produces the desired shape for the support structure. The support structure is also biocompatible (e.g., not toxic to the cells suspending in the hydrogel) and, in some cases, the support structure can be biodegradable. The support structure can be shaped either before or after the hydrogel-cell composition fills the support structure. For example, a partially flexible support structure can be filled with the hydrogel-cell composition and molded into a desired shape, e.g., by hand, as the hydrogel hardens.

In some cases, it is desirable that the support structure be flexible and/or compressible and resilient. In particular, in these cases, the support structure can be deformed as it is implanted, allowing implantation through a small opening in the patient or through a cannula or instrument inserted into a small opening in the patient. After implantation, the support structure expands into its desired shape and orientation.

The hydrogel-cell composition can be injected into the support structure either before or after the support structure is implanted into a patient. As the hydrogel solidifies, it will adopt the flexibility and resiliency of the support structure. Such resiliency and flexibility allows a support structure that is saturated with hydrogel-cell composition to accommodate compressive and tensile forces. For example, a tissue replacement for a tendon, ligament, meniscus, or piece of skin can accommodate tensile forces associated with pulling and stretching the tissue replacement and can also accommodate compressive forces associated with weight bearing by the tissue replacement. In addition, the flexibility and resiliency of the support structure can accommodate minimally invasive delivery of the tissue replacement, e.g., the support structure can be compressed and pushed into the patient through a cannula, and subsequently allowed to expand once positioned within the patient.

The support structure can be formed of a biocompatible, or biodegradable, synthetic polymer such as a polyanhydride, polyorthoester, or polyglycolic acid. The polymer should be chosen so that the resulting support structure provides adequate shape and support for the cell-containing hydrogel suspension and allows nutrients to diffuse to the cells and promote cell growth and proliferation. Factors, including nutrients, growth factors, inducers of differentiation or dedifferentiation, products of secretions, immunomodulators, inhibitors of inflammation, regression factors, biologically active compounds which enhance or allow ingrowth of the lymphatic network or nerve fibers, and drugs, can be incorporated into the polymer support structure. An example of a suitable polymer is polyglactin, which is a 90:10 copolymer of glycolide and lactide and is manufactured as VICRYL™ braided absorbable suture (Ethicon Co., Somerville, N.J.).

Polymer fibers, such as the VICRYL™ braided absorbable suture, can be compressed together into a felt-like polymer mat, which is then cut into the desired shape to form the support structure. Alternatively, the polymer fibers can be compressed together in a mold that casts the compressed fibers into the desired shaped for the support structure. In some cases, additional polymer can be added to the polymer fibers as they are molded to impart additional structure to the fiber mesh.

For example, a polylactic acid solution can be added to a polyglycolic fiber mesh and the combination can be molded together to form a porous support structure. The polylactic acid binds the crosslinks of the polyglycolic acid fibers and coats these individual fibers, which fixes the shape of the molded fibers. The polylactic acid also fills in the spaces between the fibers. Thus, the porosity of the support structure can be specified by introducing an appropriate amount of polylactic acid. The pressures required to mold the fiber mesh into the desired shape can be quite moderate. All that is required is that the fibers are held in the desired shape for a time sufficient for the binding and coating action of polylactic acid. Suitable lengths and thicknesses of the fiber will depend on the desired shape and purpose of the support structure. For example, the strength of the fibers, which is proportional to their thicknesses, should be sufficient to resist the external forces that will be applied to that support structure.

Alternatively, or in addition, the support structure can include other types of polymer fibers, or polymer structures produced by techniques known in the art. For example, thin polymer films can be obtained by evaporating solvent from a polymer solution. These can be cast into a desired shaped if the polymer solution is evaporated from a mold having the relief pattern of the desired shape. Polymer gels can also be molded into thick, permeable polymer structures using compression molding techniques known in the art.

The support structures can also be made from porous hydroxyapatite, e.g., made from chemically-altered marine coral (e.g., Interpore®). Unaltered marine coral can be used, but is resorbed by the body. The hydroxyapatite is machined into the shape of the desired support structure using instrumentation known in the art, such as a Dremel drill. The use of hydroxyapatite or coral as the support structure is especially appropriate for growing tissue in bone defects. To deposit the hydrogel-cell composition into the coral a needle is inserted into a pore, deep into the coral, and the hydrogel-cell composition is injected as a liquid. Since pores of the coral are interconnected with one another, the liquid hydrogel-cell composition permeates through the coral and saturates the coral, providing an even distribution of cells.

The size and shape of the support structure corresponds to the size and shape of the tissue to be grown, e.g., the size and shape of a cartilage replacement, or a bone defect, or an ear or a nose. For example, a support structure for a human leg bone, which is porous in its center, can be as long and thick as a human leg bone. In such a case, the hydrogel-cell composition fills both the outer layer of the support structure and the central porous area, or it can fill only the outer layer leaving the central porous area empty to serve as a canal for delivering nutrients up to the inner wall of the tissue developing at the outer layer.

Many other types of support structures are also possible. For example, the support structure can be formed from sponges, foams, corals, biocompatible inorganic, ceramic, or metal structures having internal pores such a honeycomb structure made from, e.g., titanium, a skeleton of biodegradable fine struts, such as a mesh of interwoven polymer fibers, and a skeleton of biocompatible thick struts, such as, for example, a network of metal, inorganic, ceramic, or plastic rods. These support structures are prepared using known methods.

Hydrogels

The hydrogels used to practice this invention should be biocompatible and biodegradable, preferably solidify rapidly in vivo, i.e., in about 5 minutes or less after being delivered to the implanted support structure, and should be capable of sustaining living cells.

Examples of different hydrogels suitable for practicing this invention, include, but are not limited to: (1) temperature dependent hydrogels that solidify or set at body temperature, e.g., PLURONICS™; (2) hydrogels cross-linked by ions, e.g., sodium alginate; (3) hydrogels set by exposure to either visible or ultraviolet light, e.g., polyethylene glycol polylactic acid copolymers with acrylate end groups; and (4) hydrogels that are set or solidified upon a change in pH, e.g., TETRONICS™.

Examples of materials that can be used to form these different hydrogels include polysaccharides such as alginate, polyphosphazenes, and polyacrylates, which are cross-linked ionically, or block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

Ionic Hydrogels

Ionic polysaccharides, such as alginates or chitosan, can be used to suspend living cells. In one example, the hydrogel is produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix.

Tissue precursor cells are mixed with an alginate solution, the solution is delivered to an already implanted support structure and then solidifies in a short time due to the presence in vivo of physiological concentrations of calcium ions. Alternatively, the solution is delivered to the support structure prior to implantation and solidified in an external solution containing calcium ions.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol, and glucosyl. Bioerodible or biodegradable polymers, i.e., polymers that dissolve or degrade within a period that is acceptable in the desired application (usually in vivo therapy), will degrade in less than about five years and most preferably in less than about one year, once exposed to a physiological solution of pH 6–8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622. Methods for the synthesis of the other polymers described above are known to those skilled in the art. See, for example *Concise Encyclopedia of Polymer Science and Engineering*, J. I. Kroschwitz, editor (John Wiley and Sons, New York, N.Y., 1990). Many polymers, such as poly(acrylic acid), alginates, and PLURONICS™, are commercially available.

Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

For purposes of preventing the passage of antibodies into the hydrogel, but allowing the entry of nutrients, a useful polymer size in the hydrogel is in the range of between 10,000 D and 18,500 D. Smaller polymers result in gels of higher density with smaller pores.

Temperature-Dependent Hydrogels

Temperature-dependent, or thermosensitive, hydrogels can be use in the methods of the invention. These hydrogels have so-called "reverse gelation" properties, i.e., they are liquids at or below room temperature, and gel when warmed to higher temperatures, e.g., body temperature. Thus, these hydrogels can be easily applied at or below room temperature as a liquid and automatically form a semi-solid gel when warmed to body temperature. As a result, these gels are especially useful when the support structure is first implanted into a patient, and then filled with the hydrogel-cell composition. Examples of such temperature-dependent hydrogels are PLURONICS™ (BASF-Wyandotte), such as polyoxyethylene-polyoxypropylene F-108, F-68, and F-127, poly (N-isopropylacrylamide), and N-isopropylacrylamide copolymers.

These copolymers can be manipulated by standard techniques to affect their physical properties such as porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (W/V) by dispersion at 4° C., the viscosity and the gel-sol transition temperature are affected, the gel-sol transition temperature being inversely related to the concentration. These gels have diffusion characteristics capable of allowing cells to survive and be nourished.

U.S. Pat. No. 4,188,373 describes using PLURONIC™ polyols in aqueous compositions to provide thermal gelling aqueous systems. U.S. Pat. Nos. 4,474,751, '752, '753, and 4,478,822 describe drug delivery systems which utilize thermosetting polyoxyalkylene gels; with these systems, both the gel transition temperature and/or the rigidity of the gel can be modified by adjustment of the pH and/or the ionic strength, as well as by the concentration of the polymer.

pH-Dependent Hydrogels

Other hydrogels suitable for use in the methods of the invention are pH-dependent. These hydrogels are liquids at, below, or above specific pH values, and gel when exposed to specific pHs, e.g., 7.35 to 7.45, the normal pH range of extracellular fluids within the human body. Thus, these hydrogels can be easily delivered to an implanted support structure as a liquid and automatically form a semi-solid gel when exposed to body pH. Examples of such pH-dependent hydrogels are TETRONICS™ (BASF-Wyandotte) polyoxyethylene-polyoxypropylene polymers of ethylene diamine, poly(diethyl aminoethyl methacrylate-g-ethylene glycol), and poly(2-hydroxymethyl methacrylate). These copolymers can be manipulated by standard techniques to affect their physical properties.

Light Solidified Hydrogels

Other hydrogels that can be used in the methods of the invention are solidified by either visible or ultraviolet light. These hydrogels are made of macromers including a water soluble region, a biodegradable region, and at least two polymerizable regions as described in U.S. Pat. No. 5,410, 016. For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, e.g., long wavelength ultraviolet light.

Examples of such light solidified hydrogels include polyethylene oxide block copolymers, polyethylene glycol polylactic acid copolymers with acrylate end groups, and 10K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity.

Tissue Precursor Cells

Tissue precursor cells can be obtained directly from a mammalian donor, e.g., a patient's own cells, from a culture of cells from a donor, or from established cell culture lines. Preferably the mammal is a mouse, rat, rabbit, guinea pig, hamster, cow, pig, horse, goat, sheep, dog, cat, and most preferably, the mammal is a human. Cells of the same species and preferably of the same immunological profile can be obtained by biopsy, either from the patient or a close relative. Using standard cell culture techniques and conditions, the cells are then grown in culture until confluent and used when needed. The cells are preferably cultured only until a sufficient number of cells have been obtained for a particular application.

If cells are used that may elicit an immune reaction, such as human muscle cells from an immunologically distinct donor, then the recipient can be immunosuppressed as needed, for example, using a schedule of steroids and other immunosuppressant drugs such as cyclosporine. However, the use of autologous cells will avoid such an immunologic reaction.

Cells can be obtained directly from a donor, washed, suspended in a selected hydrogel before being delivered into a support structure. To enhance cell growth, the cells are added or mixed with the hydrogel just prior to insertion into the support structure.

Cells obtained by biopsy are harvested, cultured, and then passaged as necessary to remove contaminating, unwanted cells. The isolation of chondrocytes and osteoblasts is described in the examples below.

Cell viability can be assessed using standard techniques including visual observation with a light or scanning electron microscope, histology, or quantitative assessment with radioisotopes. The biological function of the cells delivered to the support structure can be determined using a combination of the above techniques and standard functional assays.

Examples of cells that can be delivered to the support structure and subsequently grow new tissue include epidermal cells; chondrocytes and other cells that form cartilage ("cartilage-forming cells"); macrophages; dermal cells; muscle cells; hair follicles; fibroblasts; organ cells; macrophages; osteoblasts, periosteal cells, and other cells that form bone ("bone forming cells"); endothelial cells; mucosal cells, e.g., nasal, gastric, bladder and oral mucosal cells; pleural cells; ear canal cells; tympanic membrane cells; peritoneal cells; Schwann cells; corneal epithelial cells; gingiva cells; tracheal epithelial cells; and neural cells, including neuronal stem cells and neurons.

Preparation of Hydrogel-Cell Compositions

First, a hydrogel of choice is prepared using standard techniques. For example, a biodegradable, thermosensitive polymer at a concentration ranging between 5 and 25% (W/V) is useful for the present invention. If the hydrogel is an alginate, it can be dissolved in an aqueous solution, for example, a 0.1 M potassium phosphate solution, at physiological pH, to a concentration between 0.5 to 2% by weight, e.g., 1%, to form an ionic hydrogel.

Second, isolated tissue precursor cells are suspended in the polymer solution at a concentration mimicking that of the tissue to be generated, e.g., between 10 and 100 million cells/ml, most preferably between 20 and 50 million cells/ml. The optimal concentration of cells to be delivered into the support structure is determined on a case by case basis, and may vary depending on cellular type and the region of the patient's body into which the support structure is implanted. Optimization experiments require modifying only a few parameters, i.e., the cell concentration or the hydrogel concentration, to provide optimal viscosity and cell number to support the growth of new tissue.

For example, as demonstrated below, new growth of bone tissue in the shape of a rat femur, penetrating into the entire thickness of a polymeric support structure 5 mm in diameter, was observed after injecting a hydrogel-cell composition containing approximately 50 million periosteal cells per ml.

Delivery to and Implantation of the Support Structure

The liquid hydrogel-cell composition is delivered into any of the permeable support structures described herein. FIG. 1 shows a cross-sectional schematic of a filled support structure for the case of a support structure 10 formed from a mesh of interwoven polymer fibers 12. The spaces between the fibers form interconnected pores 14, which are filled with the liquid hydrogel-cell composition. Within a short time after delivery, e.g., less than three or five minutes, the hydrogel 16 solidifies, thereby keeping the cells 18 suspended in the hydrogel within pores 14 of support structure 10. The solidified hydrogel 16 keeps the cells viable, allowing diffusion of nutrients and waste products through the interconnected pores of the support structure and ultimately resulting in the growth of new tissue and its engraftment to the patient's body. The support structure 10 provides a shape and structure for the solidifying hydrogel-cell composition while still providing permeable paths for diffusion through the hydrogel. The tissue grown by the cells will conform to the shape of the support structure and the support structure will provide structural integrity sufficient to resist external stresses from the environment and surrounding tissues during growth of the new tissue.

The liquid hydrogel-cell composition can be delivered to the shaped support structure either before or after the support structure is implanted into a patient. The specific method of delivery will depend on whether the support structure is sufficiently "sponge-like" for the given viscosity of the hydrogel-cell composition, i.e, whether the support structure easily retains the liquid hydrogel-cell composition before it solidifies. Sponge-like support structures can be immersed within, and saturated with, the liquid hydrogel-cell composition, and subsequently removed from the composition. The hydrogel is then allowed to solidify within the support structure. The hydrogel-cell-containing support structure is then implanted into the patient. The support structure can also be implanted into the patient before the hydrogel completely solidifies. Alternatively, a sponge-like support structure can be injected with the liquid hydrogel-cell composition, either before or after the support structure is implanted in the patient. The hydrogel-cell composition is then allowed to solidify. The volume of the liquid hydrogel-cell composition injected into the support structure is typically less than, but somewhat comparable to the volume of the support structure, i.e., the volume of the desired tissue to be grown.

Support structures that do not easily retain the liquid composition require somewhat different methods. In these cases, for example, the support structure is immersed within and saturated with the liquid hydrogel-cell composition, which is then allowed to partially solidify. Once the cell-containing hydrogel has solidified to the point where the support structure can retain the hydrogel, the support structure is removed from the partially solidified hydrogel, and, if necessary, partially solidified hydrogel that remains attached to the outside of the support structure is removed, e.g., scraped off the structure. Alternatively, the liquid hydrogel-cell composition can be delivered into a mold containing the support structure. For example, the liquid hydrogel-cell composition can be injected into an otherwise fluid-tight mold that contains the support structure and matches its outer shape and size. The hydrogel is then solidified within the mold, e.g., by heating, cooling, light-exposure, or pH adjustment, after which time the hydrogel-cell-containing support structure is removed from the mold and is ready to be implanted into a patient.

In other embodiments, the support structured is implanted into the patient, e.g., subcutaneously or subdermally, and thereafter, the liquid hydrogel-cell composition is delivered to implanted support structure, for example by injection through a syringe or endoscopic instrument. The volume of hydrogel-cell composition injected into the support structure should approximate the size of the support structure (i.e., the volume displaced by the desired tissue to be grown). The implanted support structure provides space and a structural template for the injected liquid hydrogel-cell composition. As described above, some of the hydrogel-cell composition may leak from the support structure prior to solidifying. However in this embodiment, existing tissue (e.g., muscle, bone, cartilage) surrounding the implanted support structure would sufficiently constrain the liquid hydrogel-cell composition within the support structure until it gels. In other embodiments, such as a tissue replacement for skin, the support structure can be externally attached to the patient, e.g., by suturing or adhesives.

In any of the above cases, the hydrogel is solidified using a method that corresponds to the particular hydrogel used (e.g., gently heating a composition including a PLURONIC™ temperature-sensitive hydrogel).

To implant the support structure, the implantation site of the mammalian patient can be exposed by surgical resection and the support structure implanted directly at that site. Alternatively, the implantation site can be viewed with the aid of, e.g., an endoscope, laparoscope, arthroscope, or esophagoscope, all of which can be modified to include a mechanical articulation and delivery system for implanting the support structure through a small incision. During implantation, the site is cleared of bodily fluids including blood, e.g., with a burst of air or suction. Thus, the hydrogel-cell-containing support structure can be introduced through a laparoscope, endoscope, laryngoscope, cystoscope, proctoscope, or thoracoscope to any the interior surface of any lumen or cavity, or other surfaces, such as intraperitoneal, extraperitoneal, and thoracic cavity, and then implanted into the desired space.

Throughout the procedure, the amount of trauma caused to the cells during the delivery and implantation steps can be determined by measuring a biological function specific for the cells being used. For example, when chondrocytes are being applied, the integrity of the new cartilage can be evaluated by standard biomechanical stress analyses, such as determination of compression moduli.

It is important to note that in addition to providing a direction and pathway for the growth of new tissue, the support structure can also alter external stresses imparted to the developing tissue. In particular, the support structure can transmit or relieve external stresses along selected directions, which can optimize tissue development. For example, the support structure can resist compressive forces, and thereby relieve compressive forces on bone tissue developing within the support structure. At the same time, the new bone cells develop under normal stresses, e.g., those produced by walking, thereby forming stronger bone tissue than bone tissue grown absent any load forces.

Also, the support structure can transmit external tensile forces imparted by stretching or twisting motions to developing tendon or ligament tissue. Such tensile forces promote the growth of tendon and ligament tissue and generate tissue that is stronger than tissue grown absent such forces.

The positioning of the support structure within the patient and the internal construction of the support structure determines how the support structure will couple external forces to the developing tissue. For example, polyglycolic fibers used to construct a support structure can be oriented along a preferred direction so that the mechanical properties of the support structure are anisotropic. In such examples, the anisotropic properties of the support structure may affect the development of different fascial planes, the orientation of bundles in tissue, such as muscular bundles in skeletal tissue and cardiac muscle, the conducting system within the cardiac muscle, and the development of polar tissues such as neurons.

Applications

Since the hydrogel-cell composition can support many different kinds of precursor cells and the support structure can guide the development and shape of the new tissue, the method can be used in any instance in which it desirable to generate new tissue. Particular applications that are described below relate to the generation of cartilage, bone, and neural tissue.

Cartilage is a specialized type of dense connective tissue consisting of cells embedded in a matrix. There are several kinds of cartilage. Hyaline cartilage is a bluish-white, glassy translucent cartilage having a homogeneous matrix containing collagenous fibers which is found in articular cartilage, in costal cartilages, in the septum of the nose, and in the larynx and trachea. Articular cartilage is hyaline cartilage covering the articular surfaces of bones. Costal cartilage connects the true ribs and the sternum. Fibrous cartilage contains collagen fibers. Yellow cartilage is a network of elastic fibers holding cartilage cells which is found primarily in the epiglottis, the external ear, and the auditory tube. By harvesting the appropriate chondrocyte precursor cells, any of these types of cartilage tissue can be grown using the methods of the invention.

For example, new tissue can be grown for a cartilage meniscus replacement in the knee. A biocompatible support structure having physical characteristics similar to, for example, a sponge, is cut or molded into the shape of the meniscus to be replaced. The support structure, which can also be biodegradable, is then delivered via an arthroscope into the knee joint and positioned in the proper orientation. Since the support structure is sponge-like, it can be compressed as it is being delivered through the arthroscope and will re-expand when properly positioned in the knee. Thereafter, a liquid hydrogel-chondrocyte composition is injected into the sponge, filling the pores of the support structure. The hydrogel subsequently solidifies, taking the shape of the desired meniscus replacement and providing a suspension for the chondrocytes that permits diffusion of nutrients and waste products to and from the suspended chondrocytes. Over time, e.g., over a period of approximately six weeks, the suspension will become vascularized and the chondrocytes will grow new cartilaginous tissue that takes the shape of the meniscus and engrafts to existing tissue.

In another example, periosteal cells (i.e., bone-growing cells) can be used in the invention to fill bone defects or to prepare entire new bones. First, the support structure is sized to the dimensions of the bone defect. The support structure can be formed from polymer fibers and cut or molded into the desired size and shape, or alternatively, the support structure can be formed from a piece of hydroxyapatite or coral and machined into the desired size and shape. The hydrogel-periosteal-cell composition can then be delivered to the support structure either before or after it is positioned within the bone defect. If necessary, adhesives can be used to adhere the support structure to the bone within the bone defect. Once again the hydrogel solidifies and suspends and maintains the cells, which subsequently grow bone tissue and fill in the bone defect. In some cases, the support structure allows some partial weight bearing even before the new bone tissue is completely grown.

In other examples, the hydrogel-cell composition can include cells that generate central nervous tissue, including brain tissue, spinal cord tissue, and peripheral nerves. The support structure can be implanted into a patient having a spinal cord or brain defect following a stroke or other injury, and the hydrogel-cell composition can be injected into the support structure. The support structure then guides the growth and development of the newly-generated neural tissue.

EXAMPLES

The present invention will be further understood by reference to the following non-limiting examples.

Example 1

Preparation of a Calcium-Alginate-Chondrocyte Composition

A calcium alginate mixture is obtained by combining calcium sulfate, a poorly soluble calcium salt, with a 1% sodium alginate dissolved in a 0.1 M potassium phosphate buffer solution (pH 7.4). The mixture remains in a liquid state at 4° C., and until its temperature is increased to over 15° C. Chondrocytes are isolated from cartilage tissue, e.g., the articular surface of calf forelimbs, using standard techniques, and are added to the mixture to generate a final cellular density of about 2 to $5 \times 10^7$/ml (e.g., representing approximately 10% of the cellular density of human juvenile articular cartilage). Such a mixture can be delivered into a permeable support structure.

Example 2

Preparation of a Thermosensitive Hydrogel-Chondrocyte Composition

A biocompatible, biodegradable, reverse-thermosensitive copolymer gel was obtained by preparing a 30% weight/volume solution of a PLURONIC™ F127, F68 block copolymer (available from BASF). The solution remains in a liquid state at less than 15° C., and solidifies within 5 to 10 minutes as the temperature is increased to over 15° C. Chondrocytes were isolated from the articular surface of calf forelimbs using standard techniques, and added to the hydrogel mixture to generate a final cellular density of about 2 to $6 \times 10^7$/ml. Such a mixture can be delivered into a permeable support structure.

Example 3

Guided Tissue Growth of a Distal Femur in a Rat Using a Permeable Support Structure In this example, a synthetic, biocompatible polymer support structure was used to guide the development of new bone tissue formed from a hydrogel-cell composition to replace the distal femur in a rat.

A rat was sacrificed and its distal femur removed. The bone was immersed into liquid in a graduated cylinder to measure the volume displaced by the bone, which was approximately 1 cc. Thereafter, an external mold of the femur was made using standard acrylic molding techniques. Using the external mold, a porous support structure composed of polyglycolic and polylactic acid was created as follows.

Figure 2:
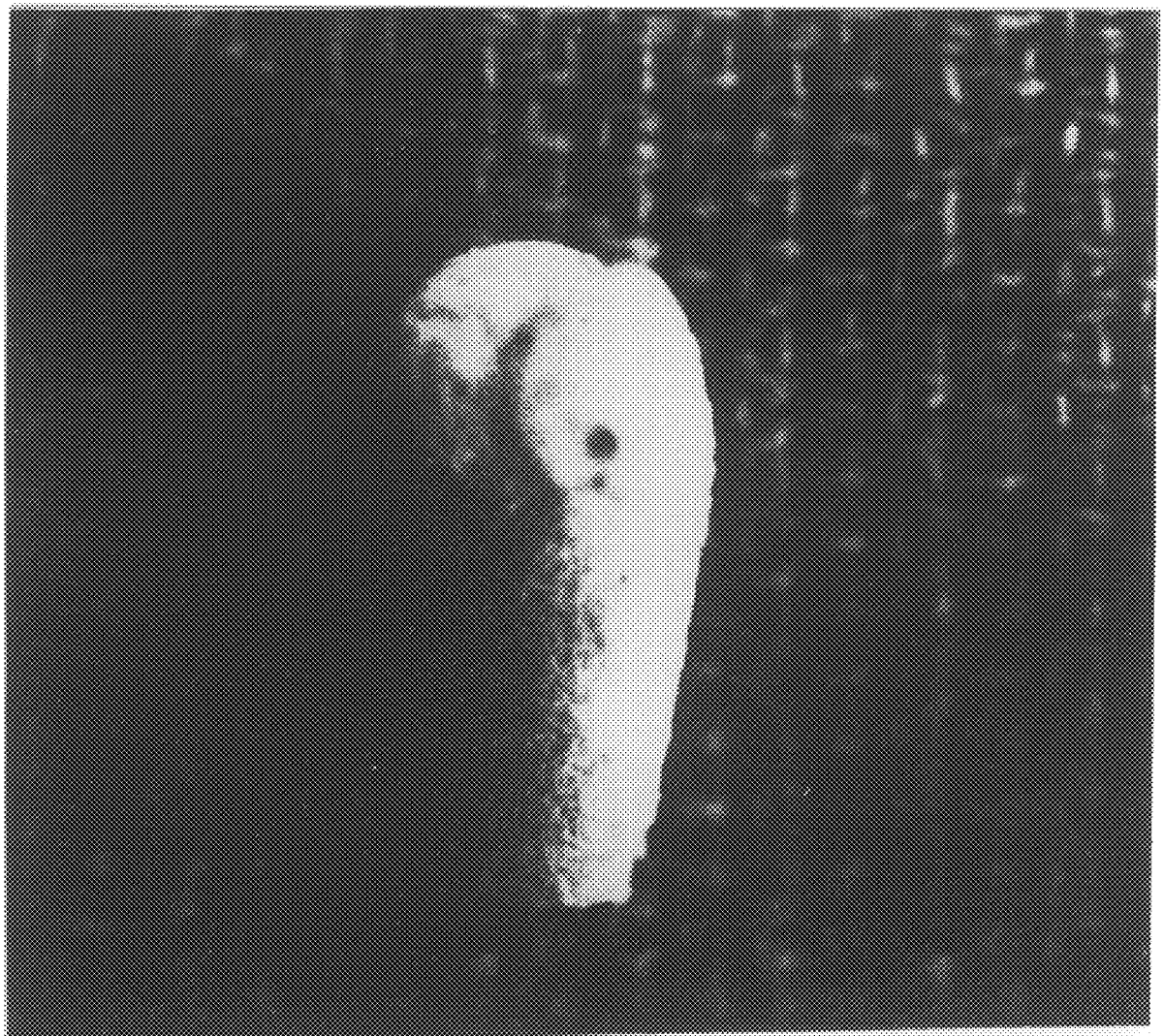
FIG. 2 is a photograph of a permeable, polymeric support structure in the shape of a rat femur.

Polyglycolic acid fibers, 14 microns in diameter, were entangled into a mesh in which the fibers are space from one another by an average of 150–250 microns. The fiber mesh was then immersed in a 1% solution of polylactic acid for about 10 seconds, when it became saturated. The solution, which has a viscosity similar to water, coated the fibers and welded the fibers to one another where the fibers intersected one another. While the fiber mesh was still wet with the polylactic acid solution, it was compressed in the mold and allowed to dry for several minutes. Once the solution evaporated and the polylactic acid dried, the fiber mesh retained the shape of the mold. The procedure took place at room temperature and produced a support structure in the shape of the distal femur with holes or pores approximately 200 microns in diameter. The femur itself was approximately 15 mm long and between 3–7 mm in diameter. FIG. 2 is a photograph of the femur support structure.

Figure 3:
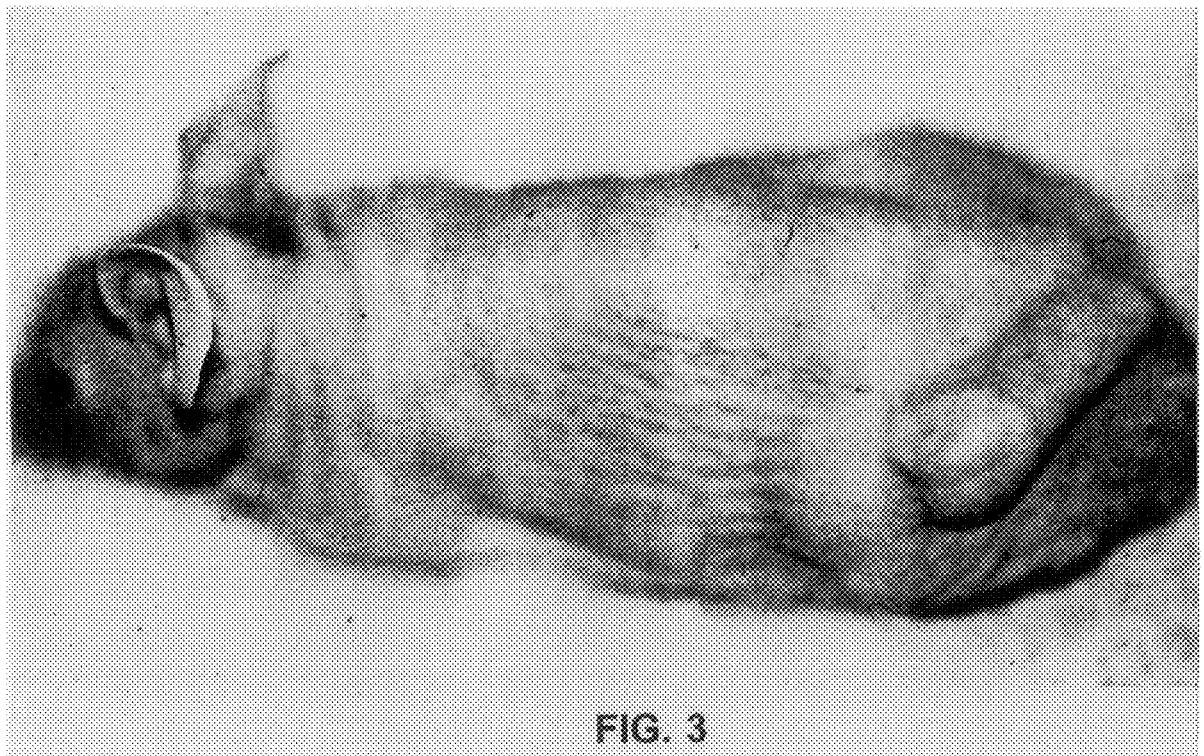
FIG. 3 is a photograph of a nude mouse in which the support structure of FIG. 2 has been implanted subcutaneously.

The support structure was then implanted subcutaneously onto the back of a nude mouse. FIG. 3 shows a photograph of the nude mouse after the support structure was implanted. The photograph clearly shows the definition of the femur-shaped support structure through the skin of the mouse. A hydrogel-cell composition containing periosteal cells was then injected into the structural support.

The periosteal cells were isolated by obtaining strips (approximately 5 mm by 3 mm) of periosteum surgically removed from the surface of a bone. The strips of periosteum were placed into a tissue culture dish containing nutrient and periosteal cells were shed from the periosteum strips and multiplied over a period of time. The cells were held in an incubator in vitro and allowed to multiply for up to 4 weeks. The hydrogel used in this example was calcium alginate, whose preparation was described in Example 1. The periosteal cells were added to the calcium alginate to produce a hydrogel-cell composition having a concentration of approximately 50 million cells per cc. A low concentration of calcium was also added to the composition.

A volume of the hydrogel-cell composition equal to the remeasured volume of the distal femur bone (approximately 1 cc) was injected through a 25-gauge needle using a 3 cc syringe into the support structure implanted under the skin of the nude mouse. The hydrogel solidified following ionic cross-linking with calcium ions, which are present in all body tissue but were also added to the hydrogel-cell composition prior to injection. After solidification of the hydrogel, the support structure allowed the cell-containing hydrogel suspension to maintain its shape and resist compressive forces while new tissue developed.

Figure 4:
FIG. 4 is a photograph of the support structure of FIG. 2 after it has been injected with a hydrogel-cell composition containing periosteal cells and subsequently removed from the mouse shown in FIG. 3.
Figure 5:
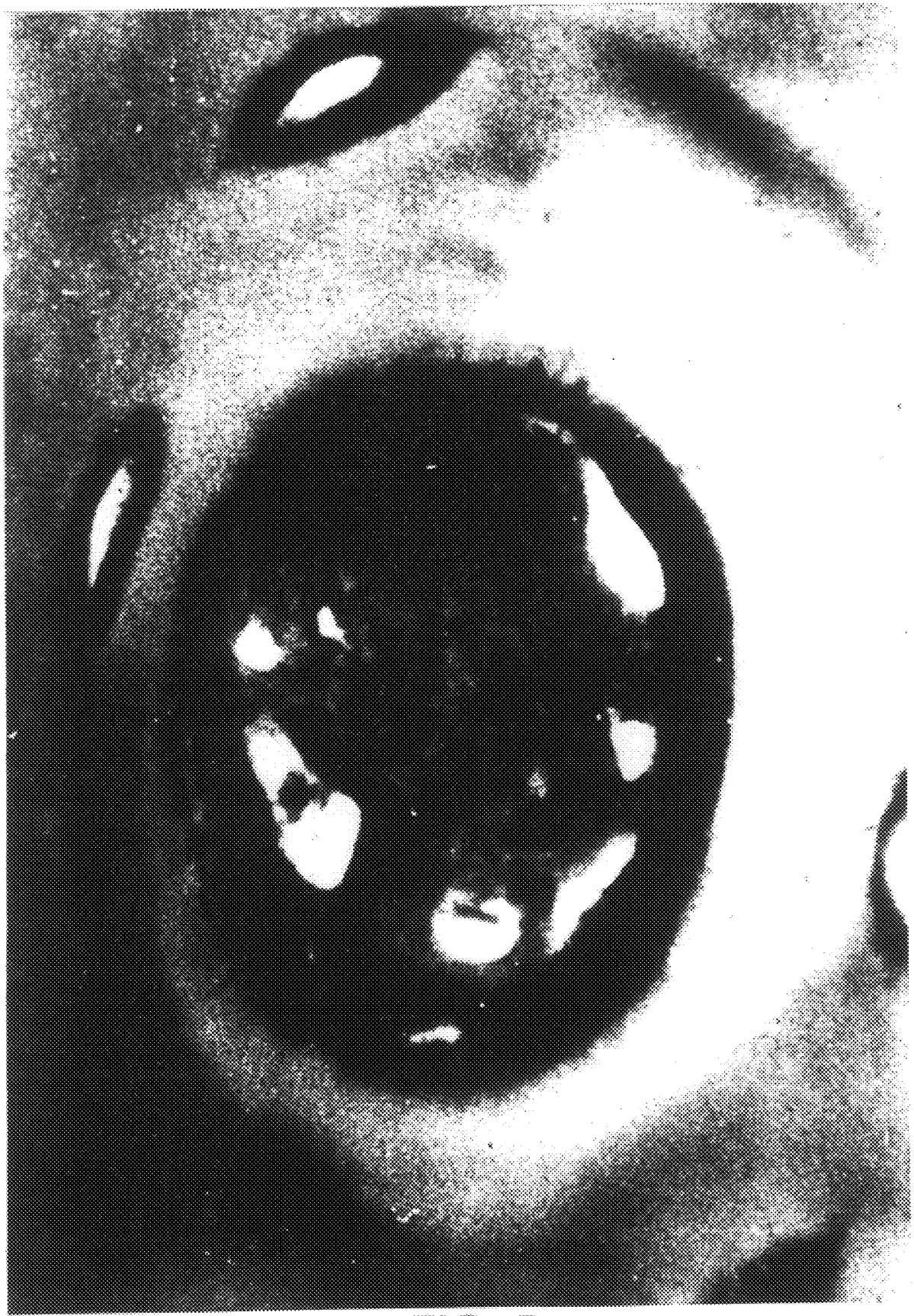
FIG. 5 is a photograph showing the histology of the support structure of FIG. 4.

After 8 weeks, the mouse was sacrificed and the femur-shaped support structure was removed for examination. As shown in the photograph in FIG. 4, new tissue engrafted to the support structure. Histological examination of the support structure, as shown in the photograph in FIG. 5, indicated new tissue growth and vascularization as indicated by the appearance of a Haversian system in the new bone. In particular, FIG. 5 shows a portion of the new tissue in which bone cells (shown in light) surround a blood vessel (shown in dark) at the center of the photograph. Additional bones cells filled the entire support structure. The photograph was taken through a 20X microscope objective and the photograph correspond to a 640 micron by 950 micron cross-sectional area.

Example 3 demonstrates that implantation of a permeable support structure having a defined shape guides the shape and development of new tissue formed from a hydrogel-cell composition injected into the support structure. The support structure resists mechanical and compressive forces and allows the cell hydrogel composition to develop new tissue of the desired shape and volume. The mouse model in this example provides evidence that the same techniques will be effective to generate new tissue in human patients.

Other Embodiments

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A method for generating new tissue, the method comprising:
   obtaining a liquid hydrogel-cell composition comprising a hydrogel and tissue precursor cells;
   delivering the liquid hydrogel-cell composition into a permeable, biocompatible support structure; and
   allowing the liquid hydrogel-cell composition to solidify within the support structure and the tissue precursor cells to grow and generate new tissue that can be vascularized.

2. The method of claim 1, wherein the delivered liquid hydrogel-cell composition is injected into the support structure.

3. The method of claim 1, further comprising implanting the support structure into an animal.

4. The method of claim 3, wherein the hydrogel-cell composition is delivered after the support structure is implanted into an animal.

5. The method of claim 1, wherein the support structure comprises a ceramic material.

6. The method of claim 1, wherein the support structure is shaped in the form of desired tissue.

7. The method of claim 6, wherein the support structure is shaped in the form of articular cartilage adjacent a joint, a bone, a portion of a bone, or a bone defect.

8. The method of claim 1, wherein the support structure is biodegradable.

9. The method of claim 1, wherein the support structure comprises a sponge or foam.

10. The method of claim 1, wherein the support structure is compressible.

11. The method of claim 1, wherein the support structure comprises a mesh of fibers.

12. The method of claim 1, wherein the support structure is rigid.

13. The method of claim 1, wherein the support structure is formed from polyanhydride, polyorthoester, polyglycolic acid, polylactic acid, or polyglactin.

14. The method of claim 1, wherein the support structure comprises porous hydroxyapatite.

15. The method of claim 1, wherein the hydrogel is selected from the group consisting of polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

16. The method of claim 1, wherein the tissue precursor cells are selected from the group consisting of epidermal cells, chondrocytes, cartilage forming cells, macrophages, dermal cells, muscle cells, hair follicles, fibroblasts, organ cells, osteoblasts, bone forming cells, endothelial cells, mucosal cells, pleural cells, ear canal cells, tympanic membrane cells, peritoneal cells, Schwann cells, corneal epithelial cells, gingiva cells, neural cells, neural stem cells, and tracheal epithelial cells.

17. A tissue forming structure comprising:
- a permeable, biocompatible support structure having a predetermined shape that corresponds to the shape of desired tissue; and
- a hydrogel-cell composition at least partially filling the support structure, wherein the hydrogel-cell composition comprises a hydrogel and tissue precursor cells, and wherein the support structure is sufficiently permeable to permit the tissue precursor cells to grow, become vascularized, and generate new tissue.

18. The tissue forming structure of claim 17, wherein the hydrogel-cell composition is a solidified suspension of hydrogel supporting dispersed tissue precursor cells.

19. The tissue forming structure of claim 17, wherein the support structure comprises a ceramic material.

20. The tissue forming structure of claim 17, wherein the support structure is biodegradable.

21. The tissue forming structure of claim 17, wherein the support structure comprises a sponge or foam.

22. The tissue forming structure of claim 17, wherein the support structure is compressible.

23. The tissue forming structure of claim 17, wherein the support structure comprises a mesh of polymeric fibers.

24. The tissue forming structure of claim 17, wherein the support structure is formed from polyanhydride, polyorthoester, polyglycolic acid, polylactic acid, or polyglactin.

25. The tissue forming structure of claim 17, wherein the support structure comprises porous hydroxyapatite.

26. The tissue forming structure of claim 17, wherein the support structure comprises metal.

27. The tissue forming structure of claim 17, wherein the support structure is rigid.

28. The tissue forming structure of claim 17, wherein the hydrogel is selected from the group consisting of polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

29. The tissue forming structure of claim 17, wherein the tissue precursor cells are selected from the group consisting of epidermal cells, chondrocytes, cartilage forming cells, macrophages, dermal cells, muscle cells, hair follicles, fibroblasts, organ cells, osteoblasts, bone forming cells, endothelial cells, mucosal cells, pleural cells, ear canal cells, tympanic membrane cells, peritoneal cells, Schwann cells, corneal epithelial cells, gingiva cells, neural cells, neural stem cells, and tracheal epithelial cells.

30. A tissue forming structure of claim 17, wherein the cells are bone forming cells and the support structure comprises porous hydroxyapatite.

31. A method for generating new tissue, the method comprising:

- obtaining a liquid hydrogel-cell composition comprising a hydrogel and tissue precursor cells;
- delivering the liquid hydrogel-cell composition into a permeable, biocompatible support structure shaped in the form of desired tissue; and
- allowing the liquid hydrogel-cell composition to solidify within the support structure and the tissue precursor cells to grow and generate new tissue.

32. The method of claim 31, wherein the delivered liquid hydrogel-cell composition is injected into the support structure.

33. The method of claim 31, further comprising implanting the support structure into an animal.

34. The method of claim 33, wherein the hydrogel-cell composition is delivered after the support structure is implanted into an animal.

35. The method of claim 31, wherein the support structure is shaped in the form of articular cartilage adjacent a joint, a bone, a portion of a bone, or a bone defect.

36. A tissue forming structure comprising:
- a permeable, biocompatible support structure having a predetermined shape that corresponds to the shape of desired tissue, the support structure comprising a ceramic material; and
- a hydrogel-cell composition at least partially filling the support structure, wherein the hydrogel-cell composition comprises a hydrogel and tissue precursor cells.

37. A tissue forming structure comprising:
- a permeable, biocompatible support structure having a predetermined shape that corresponds to the shape of desired tissue, the support structure comprising a sponge or foam; and
- a hydrogel-cell composition at least partially filling the support structure, wherein the hydrogel-cell composition comprises a hydrogel and tissue precursor cells.

38. A tissue forming structure comprising:
- a permeable, biocompatible support structure having a predetermined shape that corresponds to the shape of desired tissue, the support structure comprising a mesh of polymeric fibers; and
- a hydrogel-cell composition at least partially filling the support structure, wherein the hydrogel-cell composition comprises a hydrogel and tissue precursor cells.

39. A tissue forming structure comprising:
- a permeable, biocompatible support structure having a predetermined shape that corresponds to the shape of desired tissue, the support structure comprising porous hydroxyapatite; and
- a hydrogel-cell composition at least partially filling the support structure, wherein the hydrogel-cell composition comprises a hydrogel and tissue precursor cells.

* * * * *